(12) United States Patent
Gebhard et al.

(10) Patent No.: US 7,665,181 B2
(45) Date of Patent: Feb. 23, 2010

(54) RE-CIRCULATING VACUUM APPARATUS FOR CLEANING FABRIC AND OTHER NON-TENSIONED SURFACES

(76) Inventors: Albert W. Gebhard, 2101 E. Alameda, Denver, CO (US) 80209; Donovan J. Allen, 3433 Cannon Rd., Greer, SC (US) 29651; Patricia A. Brew, 2101 E. Alameda, Denver, CO (US) 80209

( * ) Notice: Subject to any disclaimer, the term of this patent is extended or adjusted under 35 U.S.C. 154(b) by 0 days.

(21) Appl. No.: 12/115,357

(22) Filed: May 5, 2008

(65) Prior Publication Data

US 2008/0271282 A1    Nov. 6, 2008

Related U.S. Application Data

(60) Provisional application No. 60/916,126, filed on May 4, 2007, provisional application No. 60/975,489, filed on Sep. 26, 2007.

(51) Int. Cl.
*A47L 7/00* (2006.01)
*A47L 5/24* (2006.01)

(52) U.S. Cl. ............................. 15/320; 15/344

(58) Field of Classification Search ............... 15/320, 15/344; A47L 5/24, 7/00
See application file for complete search history.

(56) References Cited

U.S. PATENT DOCUMENTS

| 784,801 A | 3/1905 | Moorhead |
|---|---|---|
| 1,383,455 A | 7/1921 | Farnsworth |
| 1,611,786 A | 12/1926 | Serva |
| 5,280,667 A | 1/1994 | Coathupe |
| 5,289,610 A * | 3/1994 | Monson ................ 15/320 |
| 5,450,649 A | 9/1995 | Turnbull |
| 5,542,148 A | 8/1996 | Young |
| 5,647,092 A | 7/1997 | Miwa |
| 6,237,188 B1 | 5/2001 | Takemoto |
| 6,245,159 B1 | 6/2001 | Deng |
| 6,725,500 B2 | 4/2004 | Allen et al. |
| 6,957,472 B2 | 10/2005 | Illingworth |
| 2002/0020035 A1 | 2/2002 | Illingworth |
| 2003/0131439 A1 | 7/2003 | Wen |
| 2004/0134024 A1 | 7/2004 | Allen |

(Continued)

FOREIGN PATENT DOCUMENTS

EP    0684341    11/1995

(Continued)

OTHER PUBLICATIONS

Office Action in U.S. Appl. No. 10/647,792 dated Feb. 28, 2006.

(Continued)

*Primary Examiner*—David A Redding
(74) *Attorney, Agent, or Firm*—Margaret Polson; Oppedahl Patent Law Firm

(57) ABSTRACT

An air re-circulating vacuum for cleaning loose fabric and other non-tensioned surfaces is disclosed. The vacuum has an air intake and an air exhaust located together inside an air space to create a turbulent flow to pull air and debris through an air flow space as the air flow space is pulled over the surface to be cleaned. The vacuum can be battery powered, or powered by plugging into a standard household current.

12 Claims, 6 Drawing Sheets

U.S. PATENT DOCUMENTS

2005/0091785 A1* 5/2005 Yuen ..................... 15/350
2005/0217065 A1  10/2005 Allen et al.
2006/0213025 A1  9/2006 Sawalski

FOREIGN PATENT DOCUMENTS

| GB | 2138280 A | 10/1984 |
|---|---|---|
| JP | S48-101765 | 12/1973 |
| JP | S60-188553 | 9/1985 |
| JP | H03-162814 | 12/1991 |
| JP | H03-162817 | 12/1991 |

OTHER PUBLICATIONS

Invitation to Pay Additional Fees in related International Application No. PCT/US2008/062674 dated Sep. 9, 2008.

Office action dated Jun. 22, 2009 in related U.S. Appl. No. 11/849,012, filed Aug. 31, 2007.

* cited by examiner

RE-CIRCULATING VACUUM APPARATUS FOR CLEANING FABRIC AND OTHER NON-TENSIONED SURFACES

CROSS REFERENCE APPLICATIONS

This application is a non-provisional application claiming the benefits of provisional application No. 60/916,126 filed May 4, 2007 and of provisional application No. 60/975,489 filed Sep. 26, 2007. This application relates to U.S. Pat. No. 6,725,500 and incorporates it by reference to the extent not inconsistent with the disclosure herein.

BACKGROUND

Many products exist that can be used to apply scent to fabric, or try to get odors out of fabric or to sanitize a fabric. Examples include Febreeze®, scented sprays, Lysol® and many similar products. Although these products can make fabrics smell better between washings, they do nothing to remove loose debris from the fabric. Vacuums are well known in the art. They are used for cleaning many rigid surfaces, including floors with various coverings, walls, and furniture. One of the well known limitations of most vacuums is that they cannot be used to clean "loose" fabrics, that is fabrics that are not mounted to a surface or sewn into pillows, because the strong suction necessary to pull up debris causes the loose fabric to be pulled into the intake nozzle of the vacuum. This means that loose fabric, including, but not limited to, bedding, curtains, throw rugs and lap rugs cannot be cleaned with a vacuum cleaner. This is particularly true of light weight fabric, such as sheets, sheer curtains and the like. Therefore, these fabrics must either be washed, dry cleaned, or shaken out to remove dirt and other loose debris. Repeated washing can damage some fabrics, dry cleaning is expensive and shaking often does an incomplete job of cleaning the fabric.

Most prior vacuum systems have a non-circulating air stream. The air flow comes in to the intake, flows through the debris container and then exists through an air exhaust that is spatially removed from air intake. Therefore all of the force to lift up debris is generated by suction into the air intake. It is for this reason that loose fabrics get pulled into the intake of the vacuum.

A different type of vacuum system is disclosed in U.S. Pat. No. 6,725,500 by Allen et al. entitled Air Recirculating Surface Cleaning Device. The vacuum system disclosed in this document re-circulates the air flow in the vacuum, instead of having the air blown out the back of the vacuum. The exhaust air is directed to the surface to be cleaned in a specific manner to loosen debris. The loosened debris are then sucked up by the air intake, which is preferably at an angle to the exhaust. See, for example, FIG. 13 of Allen et al.

The foregoing example of the related art and limitations related therewith are intended to be illustrative and not exclusive. Other limitations of the related art will become apparent to those of skill in the art upon a reading of the specification and a study of the drawings.

SUMMARY

One aspect of the present device is to provide a vacuum cleaning device that can be used on loose and/or light weight fabrics.

The following embodiments and aspects thereof are described and illustrated in conjunction with systems, tool and methods which are meant to be exemplary and illustrative, not limiting in scope. In various embodiments, one or more of the above described problems have been reduced or eliminated, while other embodiments are directed to other improvements.

The present device has a re-circulating airflow. This allows the vacuum to be used to clean loose fabrics, such as sheets etc., without pulling the fabric into the air intake. A removable debris container is provided to contain the material removed by the vacuum and to allow for easy emptying when needed. In an alternated embodiment, the vacuum can have a fluid reservoir with a pump and delivery tubes to allow the user to spray scented fluid on to the fabric, or to deliver odor removing fluids, such as Febreeze®, or to deliver a sanitizer. Usefully, the device can be battery powered and small enough to be used with a single hand by most users.

In addition to the exemplary aspects and embodiments described above, further aspects and embodiments will become apparent by reference to the accompanying drawings forming a part of this specification wherein like reference characters designate corresponding parts in the several views.

Before explaining the disclosed embodiment of the present invention in detail, it is to be understood that the invention is not limited in its application to the details of the particular arrangement shown, since the invention is capable of other embodiments. Exemplary embodiments are illustrated in referenced figures of the drawings. It is intended that the embodiments and figures disclosed herein are to be considered illustrative rather than limiting. Also, the terminology used herein is for the purpose of description and not of limitation.

DETAILED DESCRIPTION OF THE DRAWINGS

Figure 1:
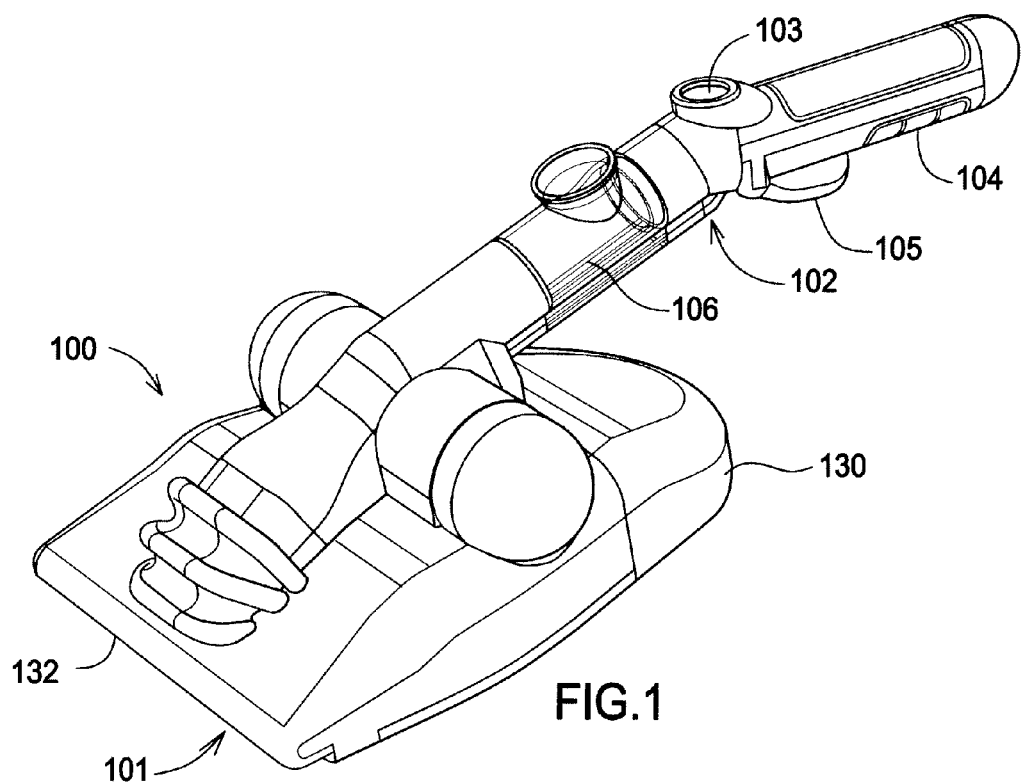
FIG. 1 is a top perspective view of the present invention.
Figure 2:
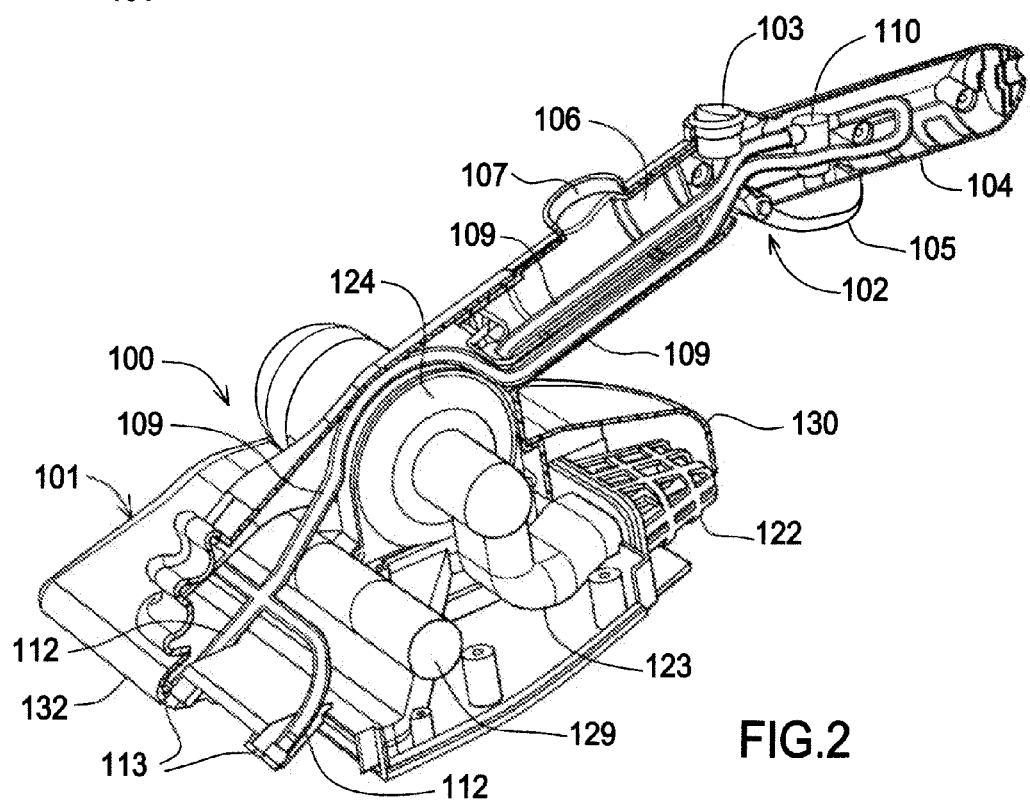
FIG. 2 is a partially cut away view of FIG. 1.
Figure 3:
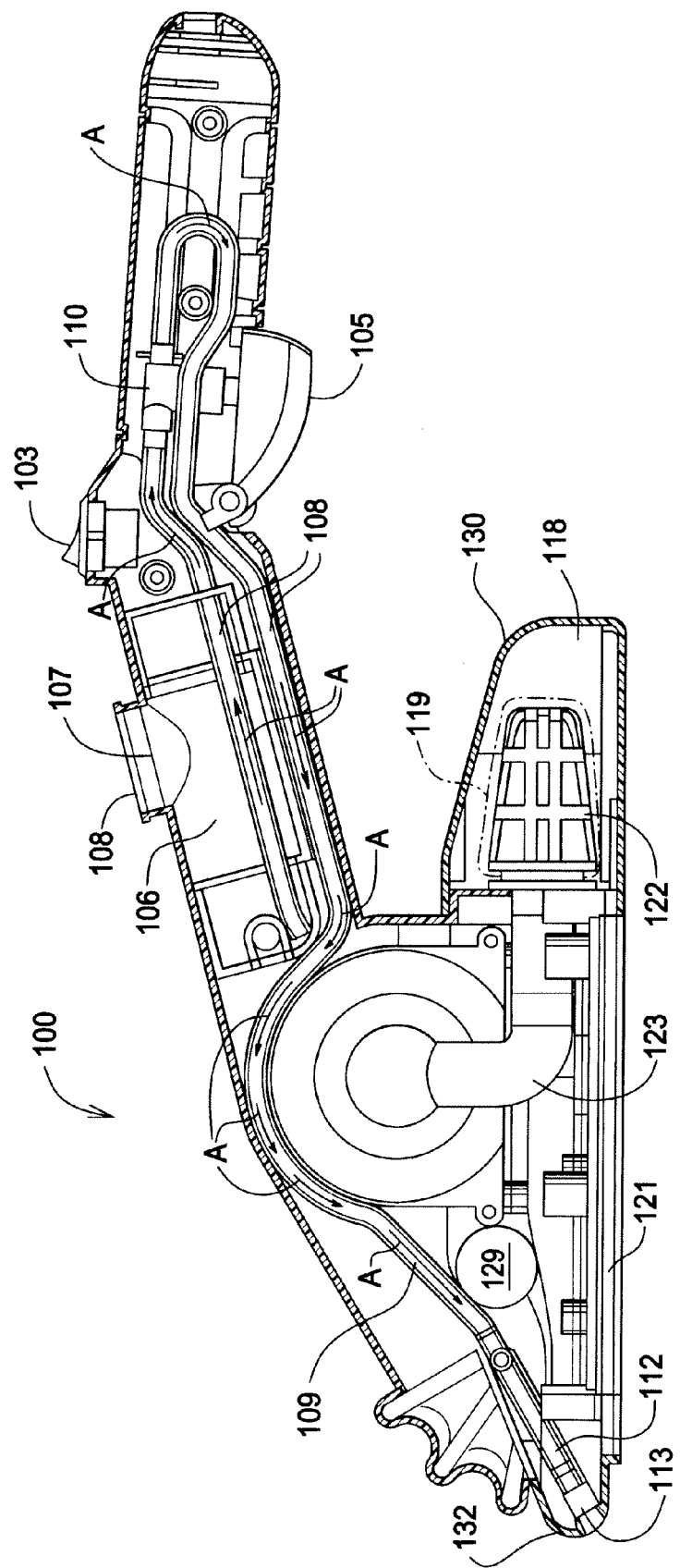
FIG. 3 is a partially cut away side elevation view of the present invention.

Referring first to FIG. 1, a vacuum 100 has a body 101 and a handle 102. The handle 102 has operating switches 103, and 105. Switch 103 controls the operation of the vacuum 100 and switch 105 controls the flow of fluid as needed. Optionally handle 102 can have a hand grip section 104 for comfort. Handle 102 has fluid reservoir 106, accessed through opening 107, which is closed with lid 108. Fluid reservoir 106 can optionally be located in the body 101 (not shown). As seen in FIGS. 2 and 3, the fluid is dispensed from reservoir 106 in tubing 109, which extends into reservoir 106. When fluid operating switch 105 is activated by a user, pump 110 is activated to pull the fluid out of reservoir 106 into the tubing 109 in the direction of arrows A seen in FIG. 3. Other known types of pumps could be used, including pump spray mechanisms and similar devices. Close to the leading edge 132 the tube 109 can split into multiple tubes 112 leading to nozzles 113. In the depicted embodiment there are three nozzles 113, it is to be understood that more or less nozzles can be used, depending in the application density of the fluid desired and the size of the leading edge 132. The nozzles 113 can spray liquid directly on the surface being cleaned (not shown) or may spray liquid in to the air flow as described below.

Figure 4:
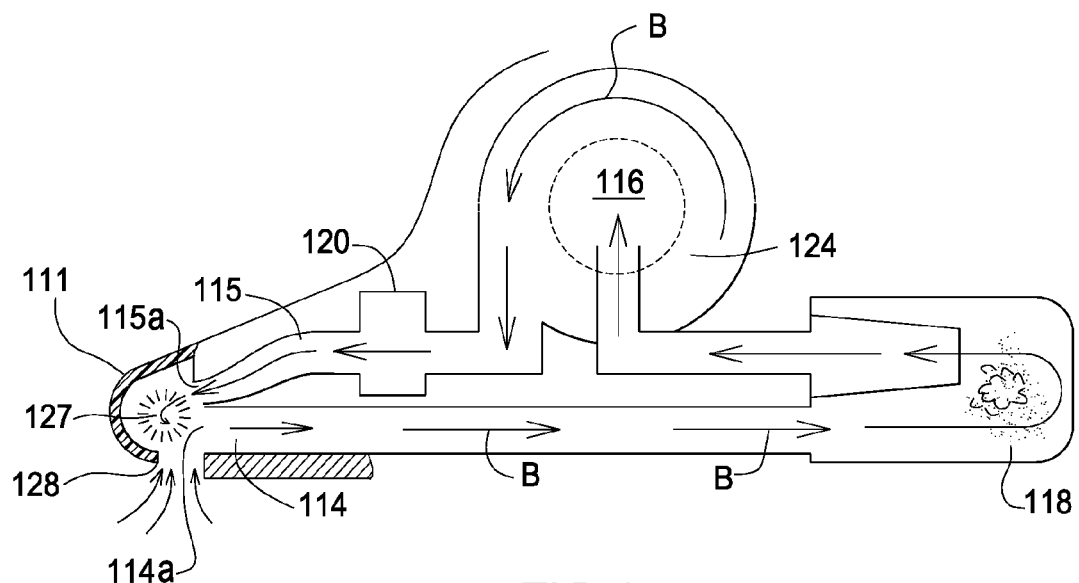
FIG. 4 is a schematic view of the air flow.
Figure 8:
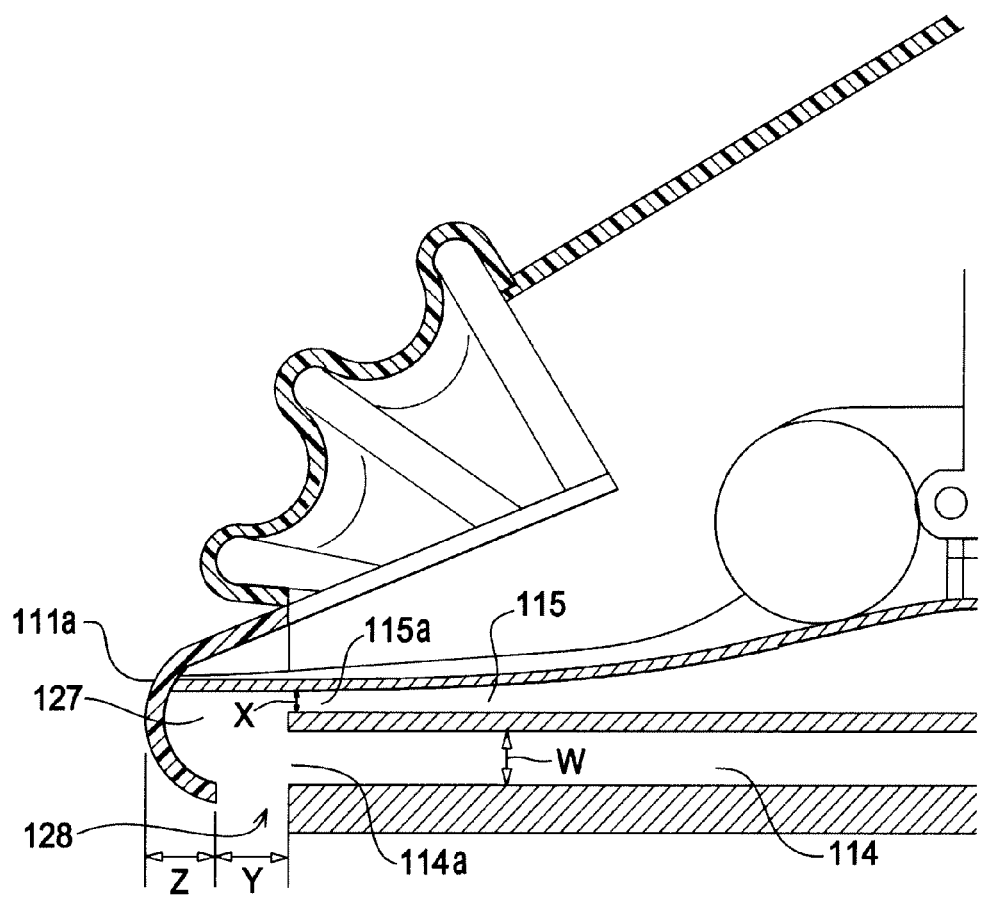
FIG. 8 is a close up view of the leading edge of the present invention.

The air flow thru the vacuum 100 is shown in schematic form in FIG. 4. The air flow is created by motor 116 and fan 117 and is shown by arrows B. The air is sucked up through air intake channel 114 into the debris chamber 118. Any particles are removed from the air flow by filter 119. The air flows up through the fan 117 to be exhausted through air exhaust channel 115 at the leading edge 32 In the depicted embodiment the air exhaust 115 has a smaller cross section than the air intake 114, 3/32 inch to 11/16 inch respectively, arrows X and W in FIG. 8. The air intake opening 114a and air exhaust opening 115a are both located near leading edge 132. In the depicted embodiment, the leading edge 132 is formed into an air dam 111. The air dam 111 is spaced apart from air intake opening 114a and air exhaust opening 115a, creating air flow space 127. The air exhaust channel 115 and opening 115a can be at an angle to the air intake channel 114 and opening 114a and spaced back from air opening 114a, as disclosed in the '500 patent to Allen.

Figure 5:
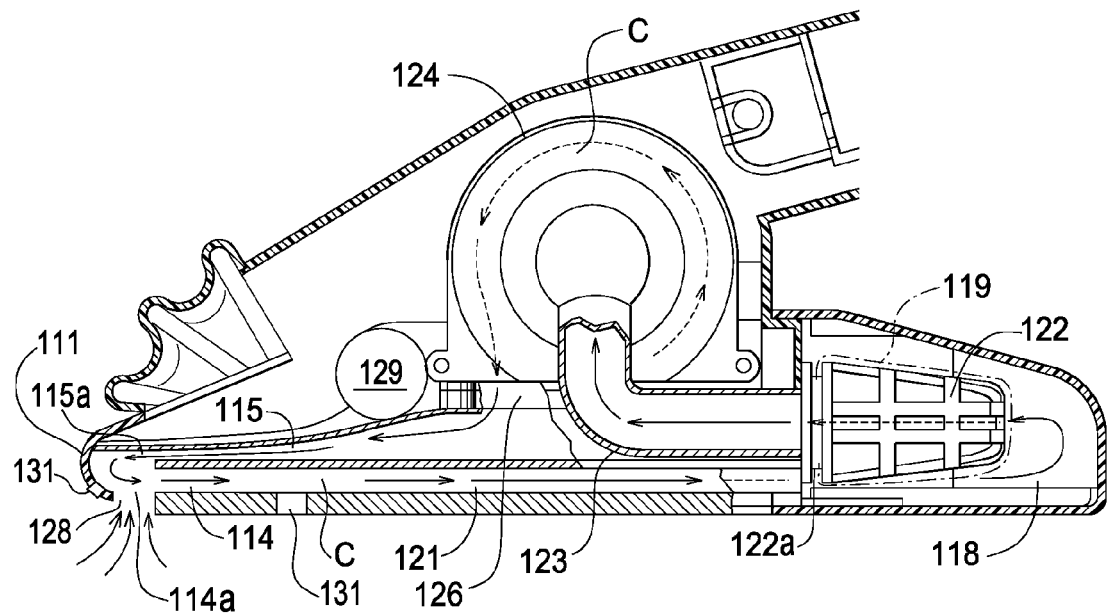
FIG. 5 is a side cut away view showing the air flow path.

Below the air dam 111 is air flow opening 128, which is the location of the air flow into the vacuum 100. In the depicted embodiment air flow opening 128 has an internal width of 3/4 inch, as shown by arrow Y in FIG. 8 and is spaced back from the front by 7/8 inch as shown by arrow Z. The operation of the air dam 111 and the air flow is explained in greater detail below. As the vacuum 100 is moved over a surface to be cleaned, air flow opening 128 is moved over the surface the air flow into air flow opening pulls loose debris of the surface to be cleaned and into the air intake channel 114. An optional filter 120 can be added into the air flow after the fan housing 124 to catch any additional particles to prevent them from being blown back onto the vacuumed surface. As seen in FIGS. 4 and 5, it air intake channel 114 remains substantially parallel to the surface to be cleaned as the air flow opening 128 is moved over the surface to be cleaned in the depicted embodiment. The air exhaust channel 115 is directly above air intake channel 114, and in the embodiment shown in FIG. 5 is substantially parallel to the air intake channel 114.

The airflow through the vacuum 100 is seen in FIG. 5. The air flow through air flow opening 128 to air intake channel 114 in to lower air flow channel 121 and then into debris chamber 118 as shown by arrows C. The air flow through air intake channel 114 and air exhaust channel 115 is held substantially parallel to each other due to the channels being substantially parallel. Basket 122 holds filter 119. The filter 119 can be a loose bag, which functions to trap the debris in the debris chamber 118. Air then flows out in to fan duct 123 up into fan housing 124. The fan (not shown) is operably attached to motor 125. The air flows around fan housing 124 and out into upper duct 126 and then into air exhaust channel 115. The air then flows out through air exhaust opening 115a into air flow space 127.

Figure 6:
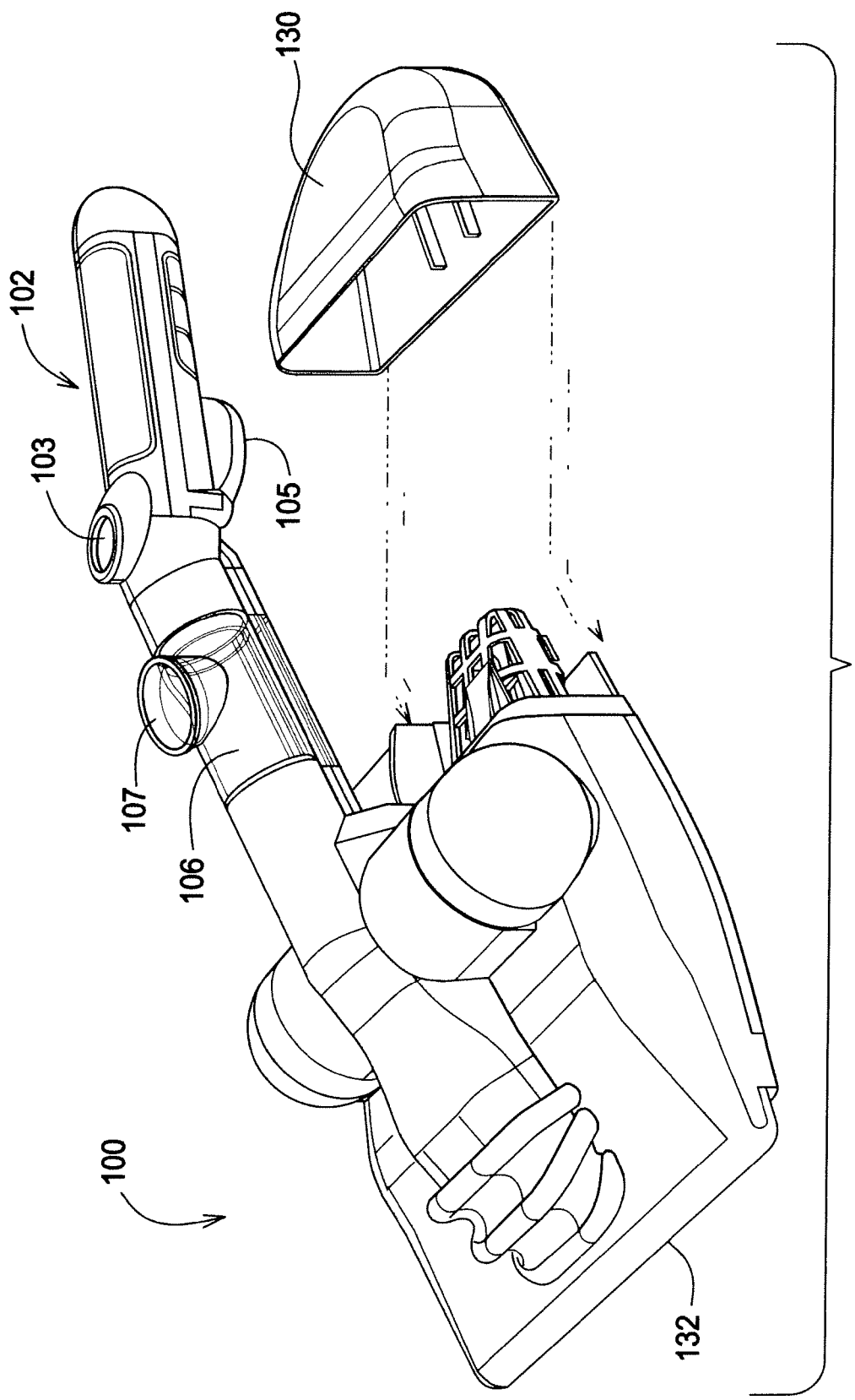
FIG. 6 is a top perspective view of the present invention with the dust bin removed.
Figure 7:
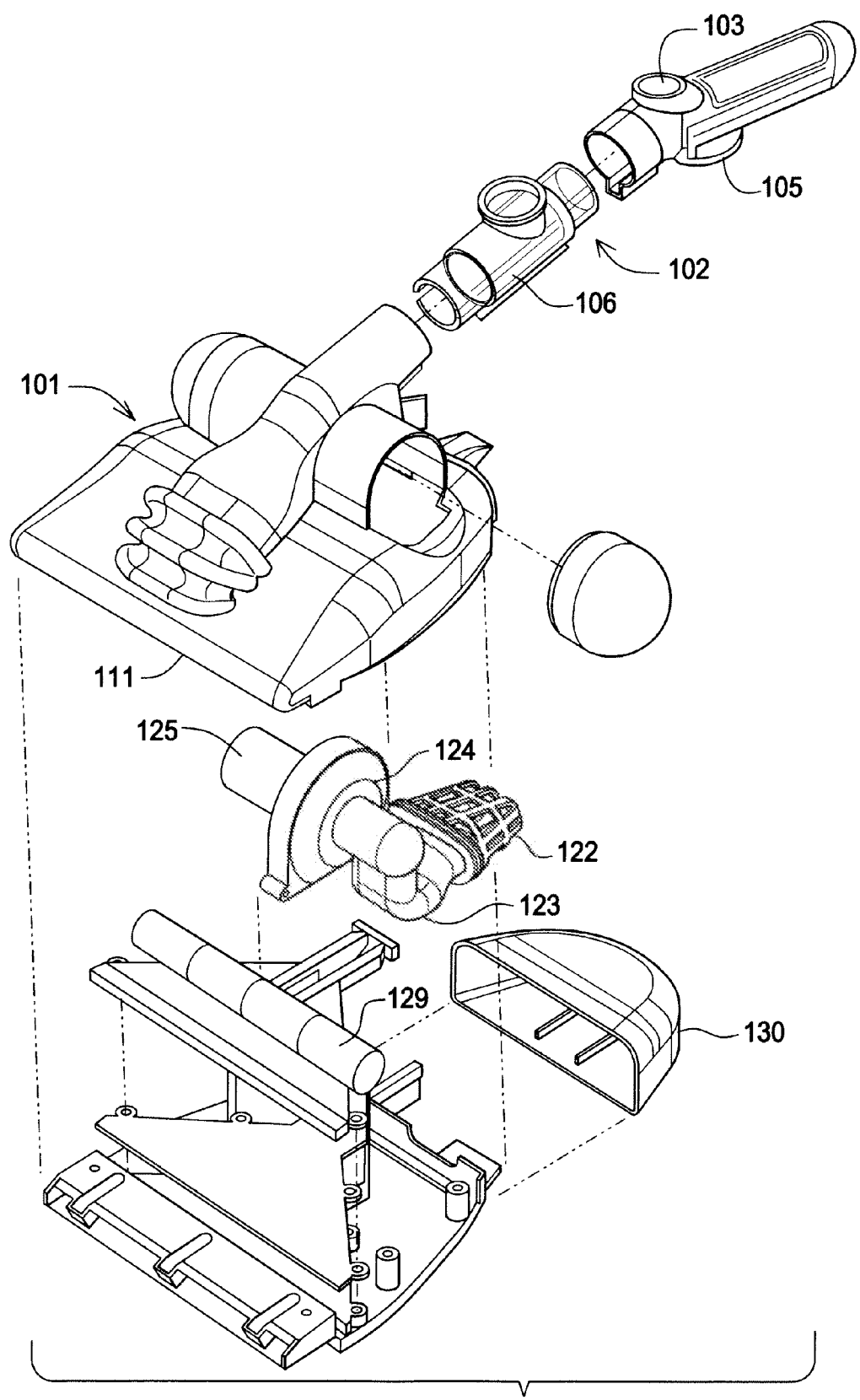
FIG. 7 is an exploded view of the present invention.

The vacuum 100 can be powered by batteries 129, which can be rechargeable, or the vacuum 100 can be plugged into a standard household outlet. Referring next to FIG. 6, the debris can be removed from the vacuum 100 by removing cover 130. Both basket 122 and filter 119 can be removable, to allow for replacement filters 119 to be used with the vacuum 100.

For additional sanitizing, a UV-C light fixture 131 can be places on the underside of the vacuum 100 as seen in FIG. 5. The antimicrobial properties of ultra violet light and the needed wavelengths and intensity to achieve the anti-microbial action are well known, and will not be further described. The light fixture 131 can be placed either in front of or behind air flow opening 128 or both, depending or design choice. The light fixture needs to be places such that the UV light will fall on the surface to be cleaned as the vacuum 100 is pulled across it in operation, other than that requirement, location of the light fixture is not constrained to the two locations in FIG. 5. A given embodiment of the vacuum 100 could have either one or more UV lights, the spraying mechanism or both, as desired for a given application.

Figure 9:
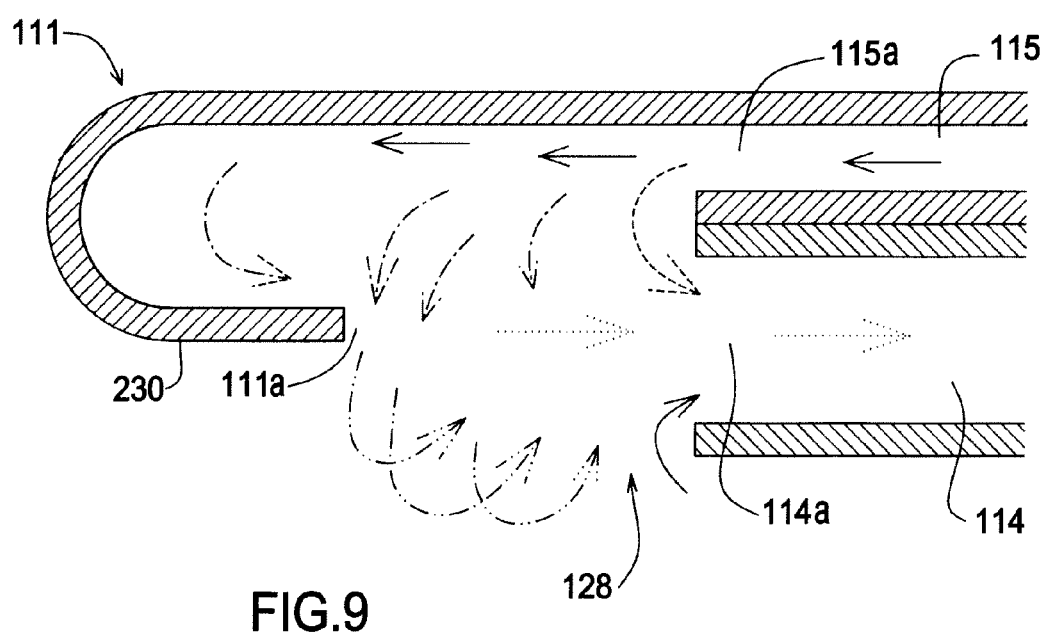
FIG. 9 is a schematic view of the air flow in the leading edge of the present invention.

FIG. 9 is a schematic drawing of the air dam 111, the air intake opening 114a, and the air exhaust opening 115a. The exact configuration of the parts with relation to each other can be varied from what is depicted in the drawings, so long as the operational affect described herein is achieved. The relative location of the pieces to each other will have to be determined experimentally for each configuration of the device. The air dam 111 curves such that the end point 11a is generally directed towards air intake opening 114a. The air flow out of air exhaust opening 115a is shown in solid arrows. Most of the air flow has too much velocity to be immediately pulled into air intake opening 114a. A portion of the air flow, shown as a dashed arrow, is pulled directly into the air intake opening 114a by the air flow into the air intake opening, shown in dotted lines. The remainder of the air flow, shown in dashed and dotted line, continues towards the air dam 111, being somewhat directed downward by the air dam 111 and the air intake air flow and is then re-directed back towards the air intake opening 1114a by the air dam 111. Some of the air flows downward out of air flow opening 128, shown by dash dot dot arrows, and as it slows, it is then pulled into air intake opening 114a. This air creates a "cushion" that prevents the suck down of a standard vacuum and allows the vacuum 100 to "float" over a surface. The air "cushion" also agitates the surface to be cleaned and the debris on the surface, causing more debris to be pulled in to the air flow into the vacuum.

While a number of exemplary aspects and embodiments have been discussed above, those of skill in the art will recognize certain modifications, permutations, additions and sub-combinations therefore. It is therefore intended that the following appended claims hereinafter introduced are interpreted to include all such modifications, permutations, additions and sub-combinations are within their true spirit and scope. Each apparatus embodiment described herein has numerous equivalents.

| List of reference symbols | |
|---|---|
| Vacuum | 100 |
| Body | 101 |
| Handle | 102 |
| Vacuum operating switch | 103 |
| Hand grip | 104 |
| Fluid operating switch | 105 |
| Fluid reservoir | 106 |
| Opening | 107 |
| Lid | 108 |
| Tubing | 109 |
| Pump | 110 |
| Air dam | 111 |
| End point | 111a |
| Tubing | 112 |
| Nozzle | 113 |
| Air intake channel | 114 |
| Air intake opening | 114a |
| Air exhaust channel | 115 |
| Air exhaust opening | 115a |
| Motor | 116 |
| Fan | 117 |
| Debris chamber | 118 |
| Filter | 119 |
| Optional filter | 120 |
| Lower air flow channel | 121 |
| Basket | 122 |
| Filter mounting groove | 122a |
| Fan duct | 123 |
| Fan housing | 124 |
| Motor | 125 |

-continued

| List of reference symbols | |
|---|---|
| Upper duct | 126 |
| Air flow space | 127 |
| Air flow opening | 128 |
| Batteries | 129 |
| Cover | 130 |
| UV light | 131 |
| Leading edge | 132 |
| Arrow A Fluid flow | |
| Arrow B Air flow | |
| Arrow C air flow | |

We claim:

1. A hand held re-circulating vacuum comprising:
a body having an upper surface, a lower surface, a leading edge, and an interior space;
a handle portion extending from at least a portion of the upper surface and having an interior space connecting with the interior space of the body;
a flow path through the interior space having an air intake opening and an air exhaust opening, both openings located proximate to the leading edge;
a vacuum blower motor operative to draw fluid into said air intake opening and expel fluid out of said an air exhaust opening;
a debris chamber in the flow path before the vacuum blower motor to receive and retain debris pulled through the air intake opening;
a flow path of intake air being substantially parallel to the surface to be cleaned for a majority of a distance to the debris chamber;
a flow path for exhaust air being substantially parallel to the surface to be cleaned for a majority of a distance from the vacuum blower motor;
a filter in the flow path between the debris chamber and the vacuum blower motor; and
a disinfecting means located proximate to the openings.

2. The hand held re-circulating vacuum of claim 1, wherein the disinfecting means comprises a fluid reservoir in the interior space fluidly connected to spray nozzles located proximate to the leading edge and an activating means to allow a user to spray a disinfecting fluid on a surface being cleaned.

3. The hand held re-circulating vacuum of claim 1, wherein the disinfecting means comprises a UV light proximate to the air openings.

4. The hand held re-circulating vacuum of claim 1 further comprising:
said air intake opening terminates substantially co-planar with the air exhaust opening;
wherein air in said air exhaust opening travels in a generally opposite direction than fluid in said air intake opening; and
an air dam is positioned in the path of air expelled from said air exhaust opening for reflecting expelled air toward said air intake opening.

5. The hand held re-circulating vacuum of claim 4, further comprising an air dam having an arcuate shape.

6. The hand held re-circulating vacuum of claim 1, further comprising an air dam which is configured to reflect air expelled from said exhaust port into a generally opposite direction.

7. The hand held re-circulating vacuum of claim 1, wherein said air exhaust channel has a reduced dimension toward said air dam.

8. A hand-held vacuum comprising:
an air exhaust channel defining a flow path therethrough, said exhaust channel having a redirection member proximate to the distal end of said flow path;
an air intake channel defining a flow path therethrough;
wherein said air exhaust channel and said air intake channel terminate in an air exhaust port and an air intake port respectively, said ports being substantially co-planar with each other and proximate to the redirection member;
said air intake channel being substantially parallel to a surface to be cleaned for a majority of a distance to a debris chamber;
said air exhaust channel being substantially parallel to the surface to be cleaned for a majority of a distance from the vacuum blower motor;
a vacuum blower motor operative to draw air into said air intake channel and expel air out of said air exhaust channel;
said redirection member being configured to reflect air expelled from said air exhaust channel toward said air intake channel such that the reflected air agitates the surface to be cleaned;
said redirection member terminating at least a given distance from the termination of the suction port; and
a disinfecting means located proximate to a leading edge of the vacuum.

9. The hand held re-circulating vacuum of claim 8, wherein the disinfecting means comprises a fluid reservoir in the interior space fluidly connected to spray nozzles located proximate to the leading edge and a activating means to allow a user to spray a disinfecting fluid on a surface being cleaned.

10. The hand held re-circulating vacuum of claim 8, wherein the disinfecting means comprises a UV light proximate to the air openings.

11. The hand held re-circulating vacuum of claim 9, wherein the spray nozzles are located on the leading edge such that the disinfecting fluid is sprayed on the surface after debris removal.

12. A hand held vacuum comprising:
a body having an upper surface, a lower surface, a leading edge, and an interior space;
a handle portion extending from at least a portion of the upper surface and having an interior space connecting with the interior space of the body;
a flow path through the interior space having an air intake opening and an air exhaust opening;
a vacuum blower motor operative to draw fluid into said air intake opening and expel fluid out of said an air exhaust opening;
a debris chamber in the flow path before the vacuum blower motor to receive and retain debris pulled through the air intake opening;
a filter in the flow path between the debris chamber and the vacuum blower motor;
a disinfecting means comprising a fluid reservoir in the interior space fluidly connected to spray nozzles located proximate to the leading edge and a activating means to allow a user to spray a disinfecting fluid on a surface being cleaned; and
spray nozzle located proximate to the air intake opening such that the disinfecting fluid is sprayed on the surface being cleaned after the surface has been cleaned of debris.

* * * * *